(12) United States Patent
Sakai et al.

(10) Patent No.: US 12,315,151 B2
(45) Date of Patent: May 27, 2025

(54) COMPUTER-READABLE RECORDING MEDIUM HAVING STORED THEREIN INFORMATION PROCESSING PROGRAM, INFORMATION PROCESSING APPARATUS, AND METHOD FOR PROCESSING INFORMATION

(71) Applicants: FUJITSU LIMITED, Kawasaki (JP); RIKEN, Wako (JP); NATIONAL CANCER CENTER, Tokyo (JP)

(72) Inventors: Akira Sakai, Kawasaki (JP); Masaaki Komatsu, Koto (JP); Kanto Shozu, Chuo (JP)

(73) Assignees: FUJITSU LIMITED, Kawasaki (JP); RIKEN, Wako (JP); NATIONAL CANCER CENTER, Tokyo (JP)

( * ) Notice: Subject to any disclaimer, the term of this patent is extended or adjusted under 35 U.S.C. 154(b) by 396 days.

(21) Appl. No.: 17/826,159

(22) Filed: May 27, 2022

(65) Prior Publication Data

US 2022/0398728 A1 Dec. 15, 2022

(30) Foreign Application Priority Data

Jun. 10, 2021 (JP) ................................. 2021-097535

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/73* (2017.01); *G06V 10/25* (2022.01);
(Continued)

(58) Field of Classification Search
CPC . G06T 7/0012; G06T 7/11; G06T 7/73; G06T 2207/30044; G06V 10/25;
(Continued)

(56) References Cited

U.S. PATENT DOCUMENTS

2010/0099987 A1  4/2010  Sasaki et al.
2020/0155114 A1  5/2020  Park et al.
(Continued)

FOREIGN PATENT DOCUMENTS

EP         3653131 A1    5/2020
JP      2000-163599 A    6/2000
(Continued)

OTHER PUBLICATIONS

Extended European Search Report issued Oct. 21, 2022, in corresponding European Patent Application 22175763.6, 5 pp.
(Continued)

*Primary Examiner* — Zhitong Chen
(74) *Attorney, Agent, or Firm* — XSENSUS LLP

(57) ABSTRACT

There is disclosed a non-transitory computer-readable recording medium having stored therein an information processing program for causing a computer to execute a process. The process includes: specifying a first region, a second region and a third region from a nondestructive inspection image, the first region corresponding to a recess-free shape, the second region corresponding to a detection target included in the recess-free shape, the third region corresponding to a reference object included in the recess-free shape; specifying a first straight line that divides the first region into two and that passes through the third region; obtaining two intersections of the first straight line and an outer circumference of the recess-free shape; specifying a second straight line that passes through a center point of the two intersections and that is orthogonal to the first straight
(Continued)

line; and outputting information indicative of a position of the detection target in the nondestructive inspection image, using a coordinate system using the first straight line and the second straight line as axes.

11 Claims, 10 Drawing Sheets

(51) Int. Cl.
  *G06T 7/73* (2017.01)
  *G06V 10/20* (2022.01)
  *G06V 10/25* (2022.01)
(52) U.S. Cl.
  CPC .. *G06V 10/255* (2022.01); *G06T 2207/30044* (2013.01); *G06V 2201/03* (2022.01); *G06V 2201/07* (2022.01)
(58) Field of Classification Search
  CPC ............. G06V 10/255; G06V 2201/03; G06V 2201/07; A61B 8/00; A61B 8/469; A61B 8/0866
  See application file for complete search history.

(56) References Cited

U.S. PATENT DOCUMENTS

| | | | |
|---|---|---|---|
| 2020/0202551 A1* | 6/2020 | Ciofolo-Veit | A61B 8/5223 |
| 2020/0226494 A1 | 7/2020 | Yasutomi et al. | |
| 2020/0234435 A1* | 7/2020 | Raynaud | G06T 7/73 |
| 2020/0401832 A1 | 12/2020 | Peng | |

FOREIGN PATENT DOCUMENTS

| | | |
|---|---|---|
| JP | 2010115483 A | 5/2010 |
| JP | 2020-113083 A | 7/2020 |
| JP | 2020527080 A | 9/2020 |
| JP | 2021-441 A | 1/2021 |

OTHER PUBLICATIONS

Japanese Office Action issued Jan. 21, 2025, in corresponding Japanese Patent Application No. JP 2021-097535, 7pp.

* cited by examiner

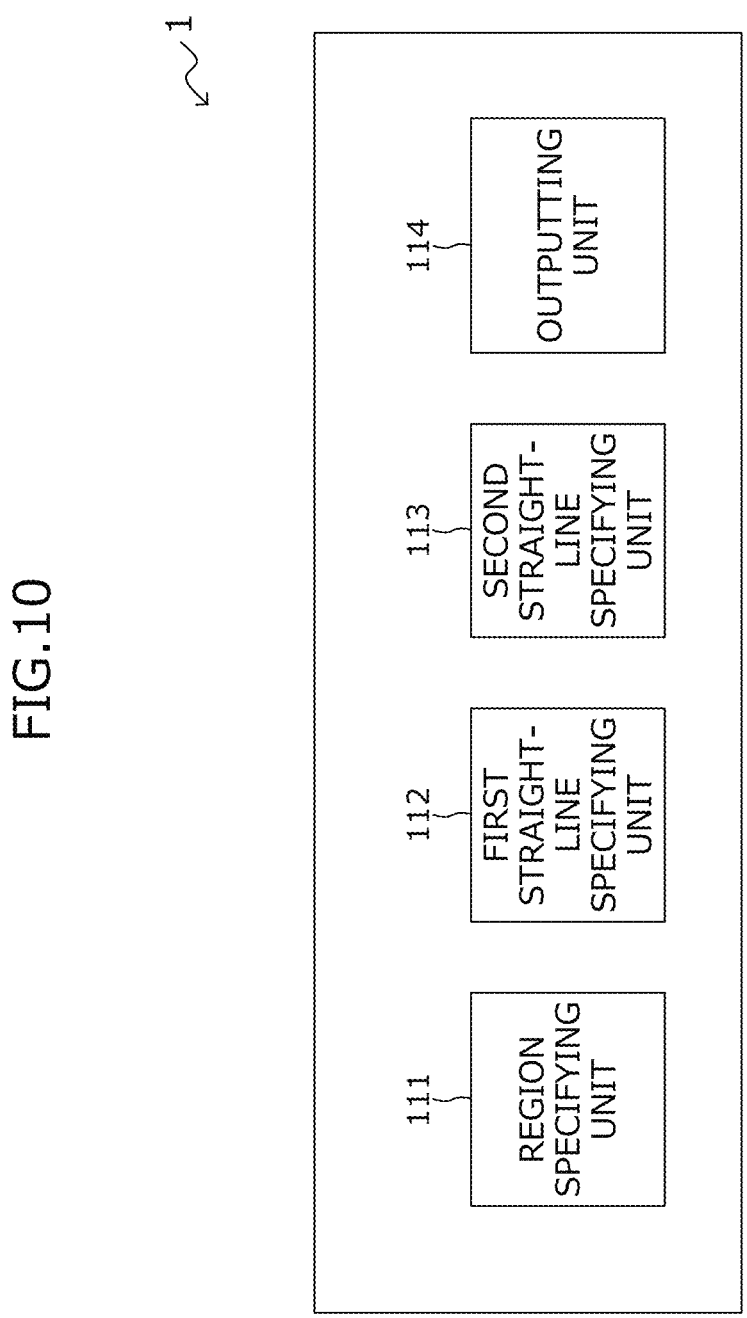

COMPUTER-READABLE RECORDING MEDIUM HAVING STORED THEREIN INFORMATION PROCESSING PROGRAM, INFORMATION PROCESSING APPARATUS, AND METHOD FOR PROCESSING INFORMATION

CROSS-REFERENCE TO RELATED APPLICATION

This application is based upon and claims the benefit of priority of the prior Japanese Patent application No. 2021-097535, filed on Jun. 10, 2021, the entire contents of which are incorporated herein by reference.

FIELD

The embodiment discussed herein relates to a computer-readable recording medium having stored therein an information processing program, an information processing apparatus, and a method for processing information.

BACKGROUND

In an ultrasonic inspection, a demand sometimes arises for grasping the relative position of a particular target to the entire object within a cross-section of the object.

For example, in ultrasonic diagnosis of a fetus, if the relative position of an organ such as the heart to the whole body can be known, the diagnosis can be useful for early detection of a disease. Besides, in an internal inspection of a clay pipe that stores the communication wiring or the like, if the position of the wiring or the like can be known, the inspection can verify whether or not the wiring or the like has distortion.

[Patent Document 1] Japanese Laid-open Patent Publication No. 2020-113083

SUMMARY

According to an aspect of the embodiments, a non-transitory computer-readable recording medium has stored therein an information processing program for causing a computer to execute a process including: specifying a first region, a second region and a third region from a nondestructive inspection image, the first region corresponding to a recess-free shape, the second region corresponding to a detection target included in the recess-free shape, the third region corresponding to a reference object included in the recess-free shape; specifying a first straight line that divides the first region into two and that passes through the third region; obtaining two intersections of the first straight line and an outer circumference of the recess-free shape; specifying a second straight line that passes through a center point of the two intersections and that is orthogonal to the first straight line; and outputting information indicative of a position of the detection target in the nondestructive inspection image, using a coordinate system using the first straight line and the second straight line as axes.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 10 is a block diagram schematically illustrating an example of a software configuration of the information processing apparatus of FIG. 9.

DESCRIPTION OF EMBODIMENT(S)

<A> Embodiment

Figure 1:
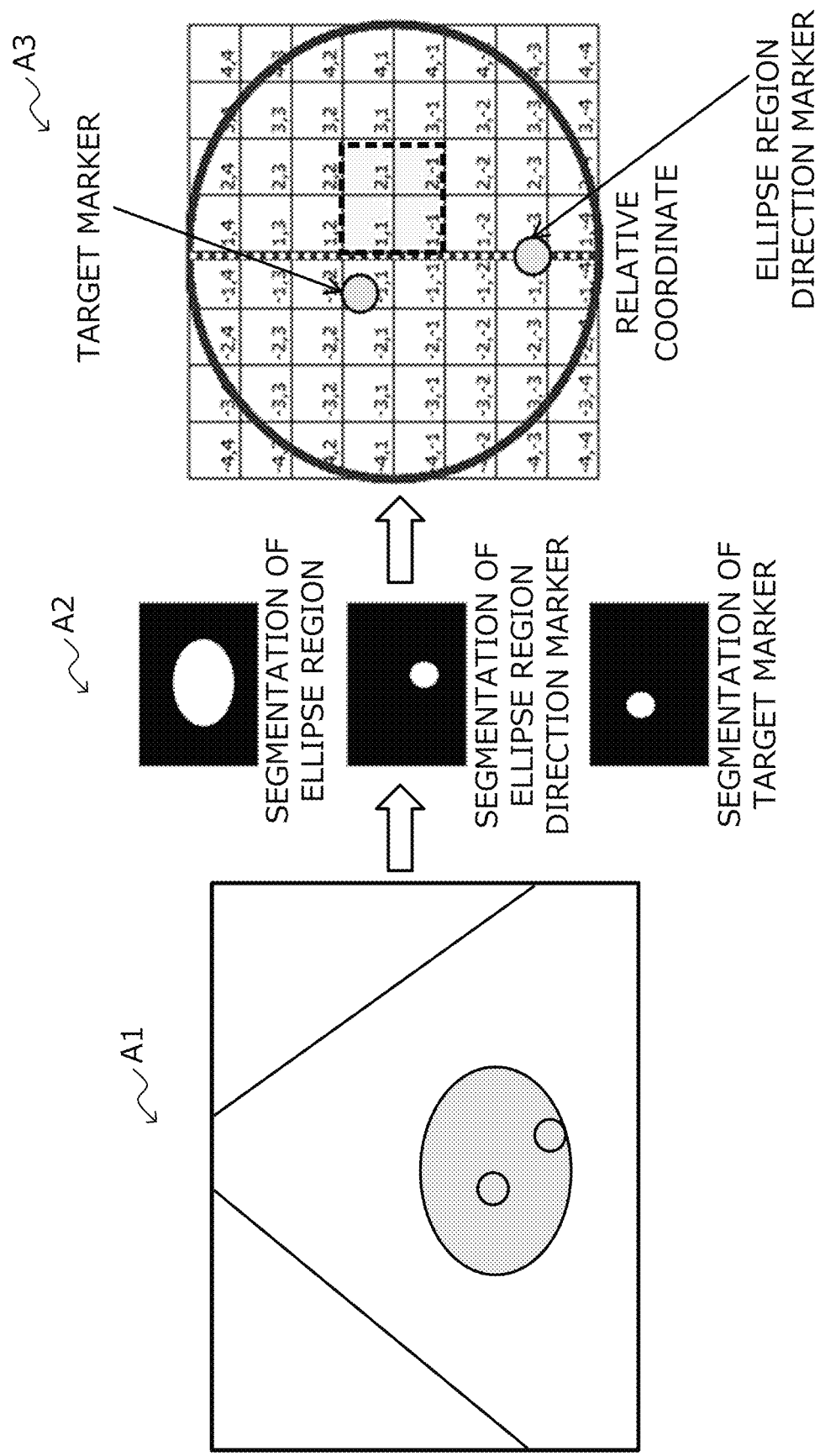
FIG. 1 is a diagram briefly illustrating a position outputting process of a target according to an embodiment.

Hereinafter, an embodiment of the present invention will now be described with reference to the accompanying drawings. However, the embodiment described below is merely illustrative and there is no intention to exclude the application of various modifications and techniques that are not explicitly described in the embodiment. For example, the present embodiment can be variously modified and implemented without departing from the scope thereof. Each drawing may include additional functions in addition to the elements appearing on the drawing.

Like reference numbers designate the same or similar parts in the drawing, so repetitious description is omitted here.

If the relative position of a specific target in the cross-section of an object to the entire object is not precisely recognized, there is a possibility of not precisely being able to evaluate the soundness or the like of the object of the inspection target.

FIG. 1 is a diagram briefly illustrating a position outputting process of a target according to an embodiment.

For a target in an ellipse region imaged by a nondestructive inspection such as ultrasonic inspection as indicated by a reference sign A1, the positions of the ellipse region, an ellipse region direction marker, and a target marker are specified by means of image segmentation as shown by a reference sign A2. Then, as indicated by the reference sign A3, the relative coordinates of the target to the ellipse region are specified by using the result of the image segmentation. The ellipse region may be any recess-free shape.

The image segmentation may be achieved by a machine learning process. A characteristic structure in the ellipse region may be utilized to determine the orientation of the ellipse region.

Figure 2:
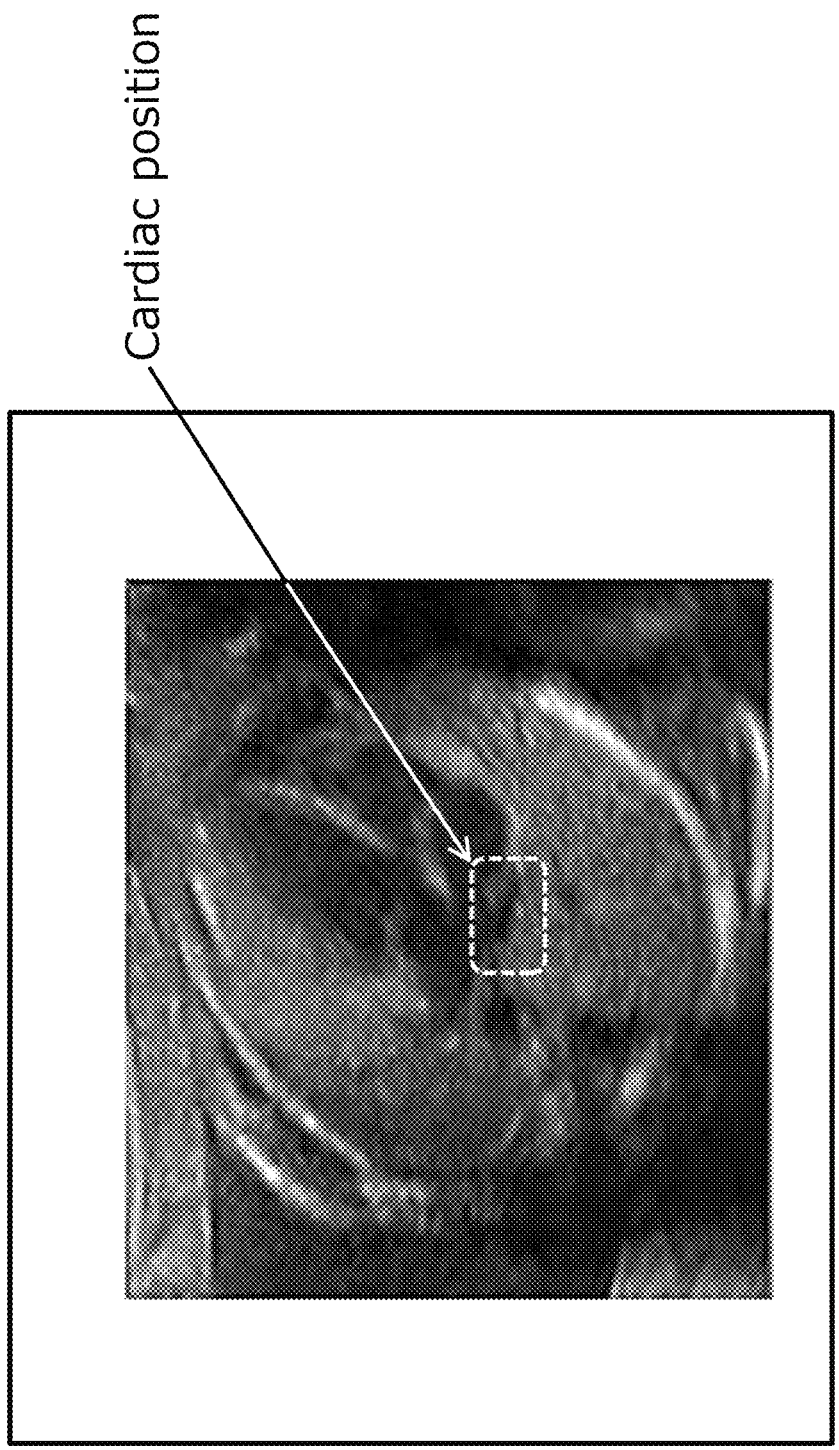
FIG. 2 is a diagram illustrating an example of an image of fetal echocardiography used in the position outputting process of the target according to the embodiment.

FIG. 2 is a diagram illustrating an example of an image of fetal echocardiography used in the position outputting process of the target according to the embodiment.

As the target of the position outputting process, a cardiac position of a fetus as illustrated in FIG. 2 may be used. The cardiac position is the position near the atrial wall of the heart. If the fetus has a heart disease, the cardiac position is misaligned and therefore comes to be a key diagnostic aid marker.

Figure 3:
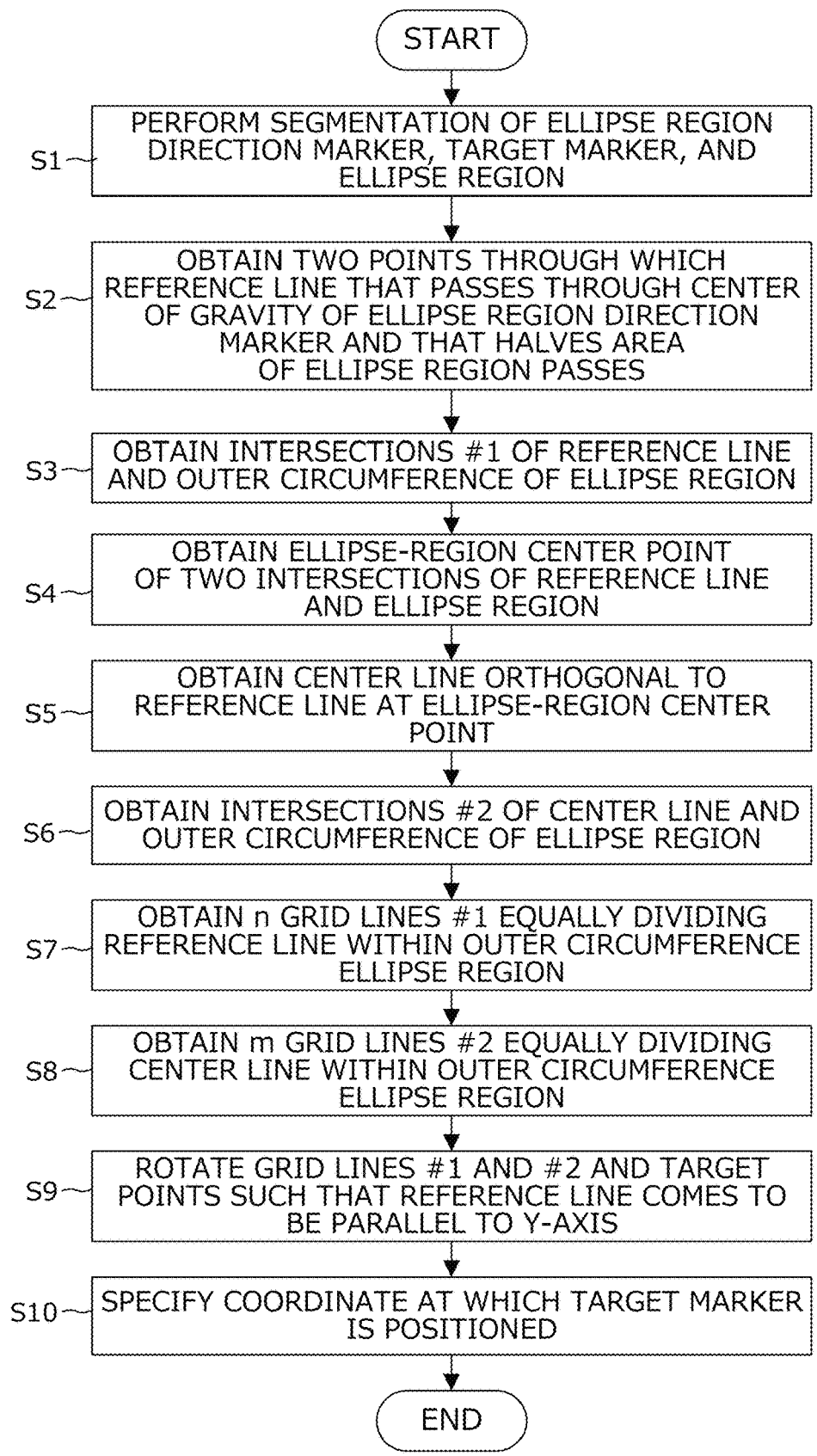
FIG. 3 is a flow diagram illustrating the position outputting process of the target according to the embodiment.
Figure 4:
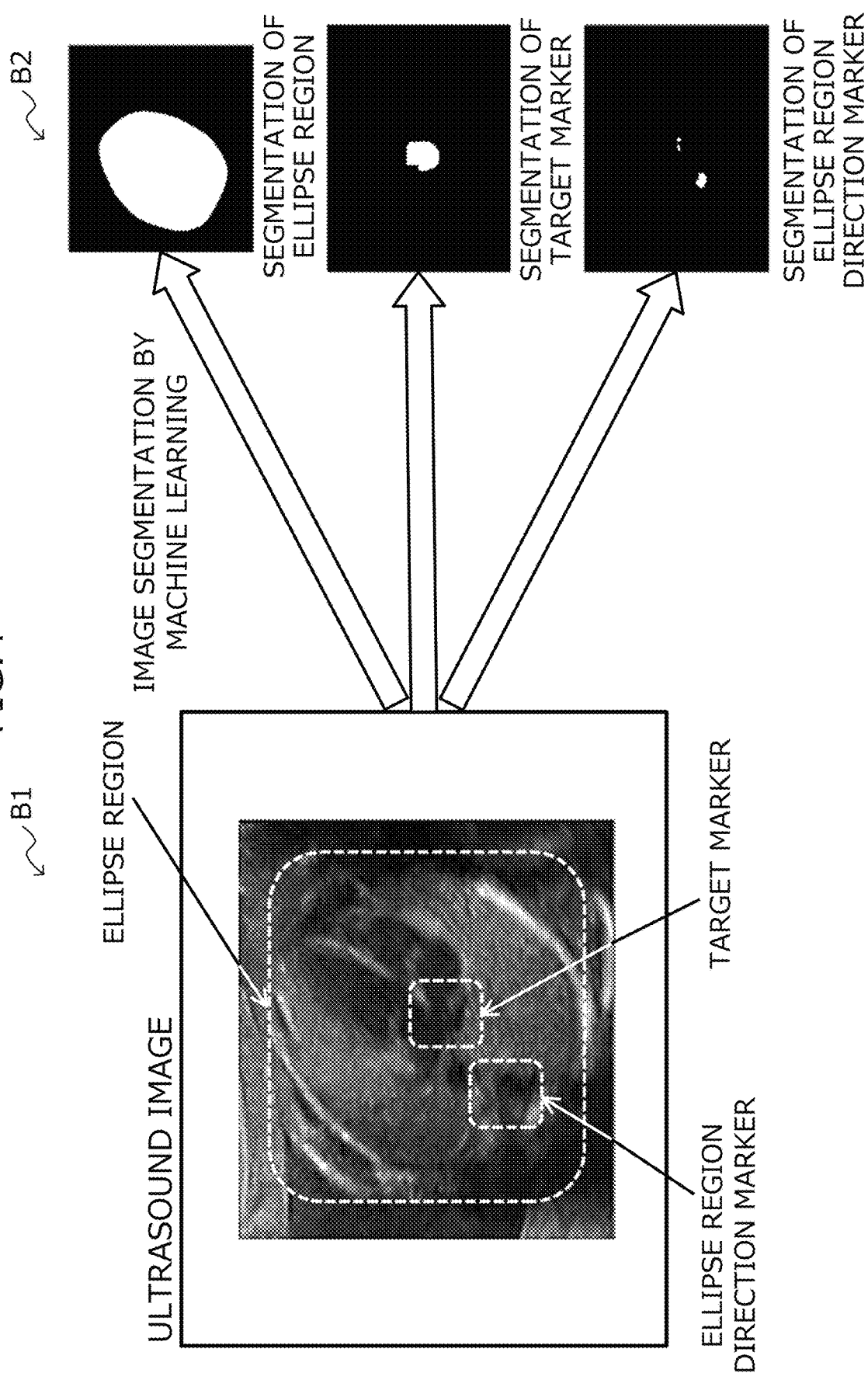
FIG. 4 is a diagram illustrating a segmentation process of FIG. 3.
Figure 5:
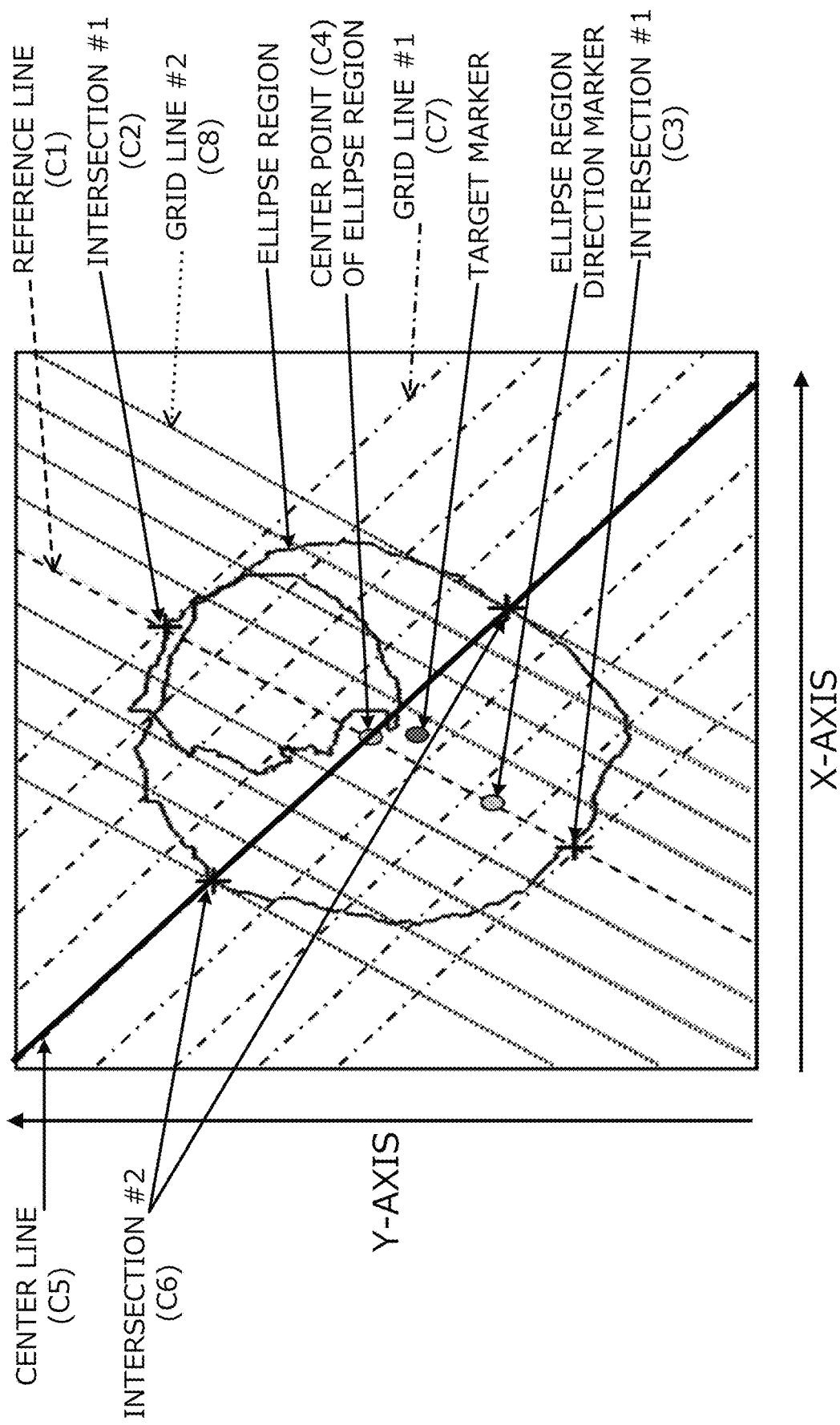
FIG. 5 is a diagram illustrating a reference line specifying process and a center line specifying process of FIG. 3.
Figure 6:
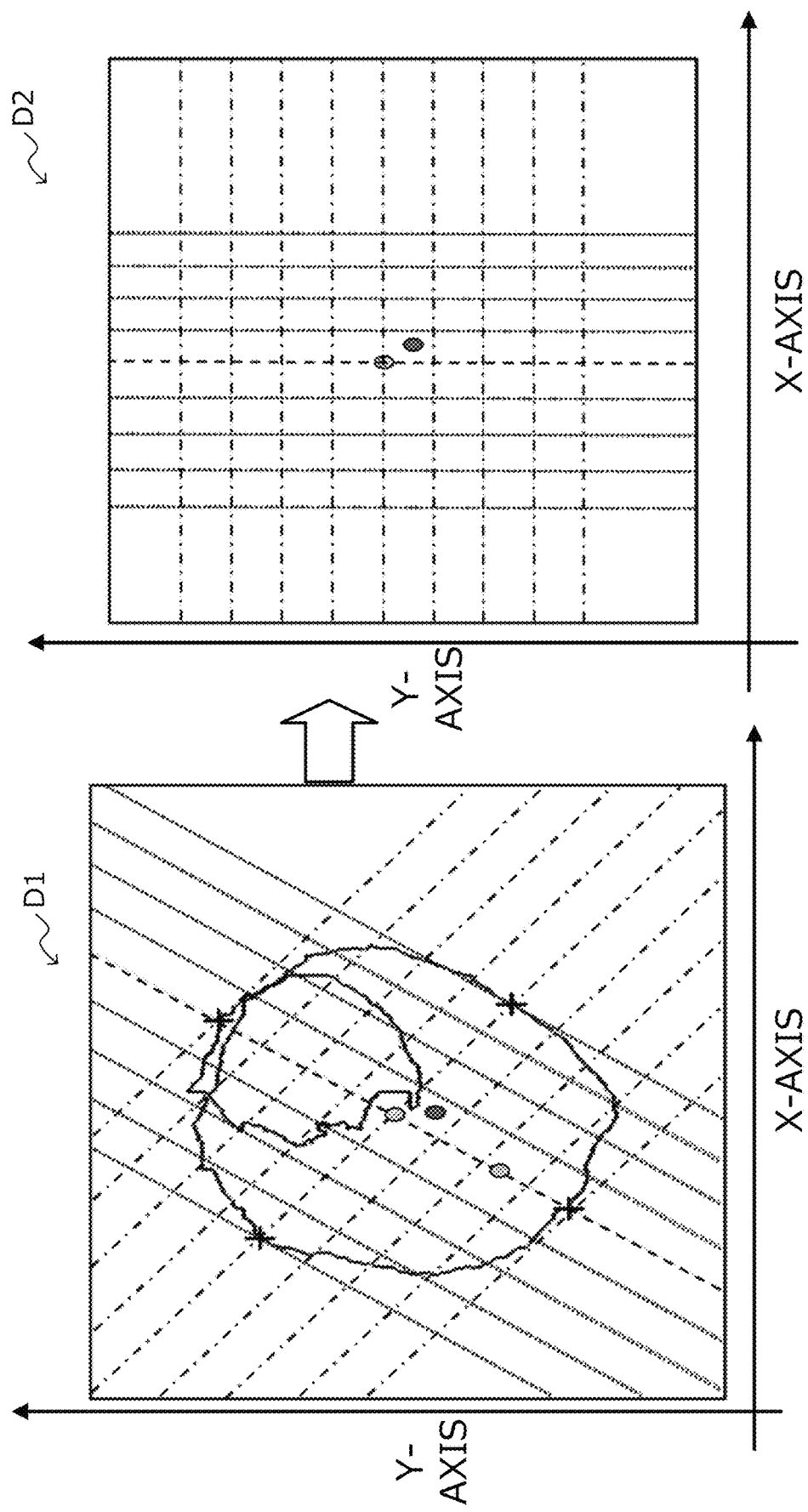
FIG. 6 is a diagram illustrating a rotating process of FIG. 3.
Figure 7:
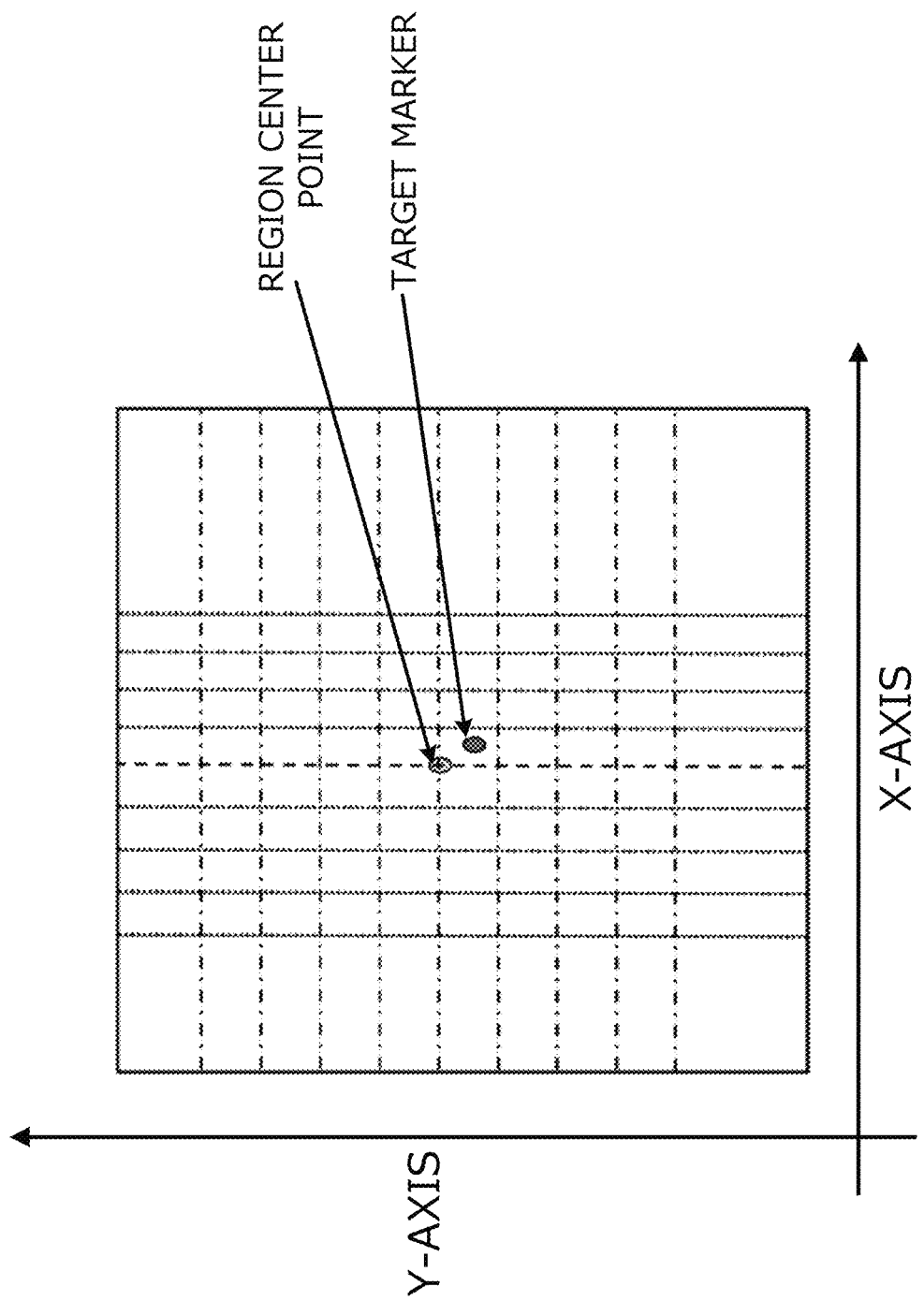
FIG. 7 is a diagram illustrating positions of a region center point and a target marker on a coordinate plane in the position outputting process of the target according to the embodiment.
Figure 8:
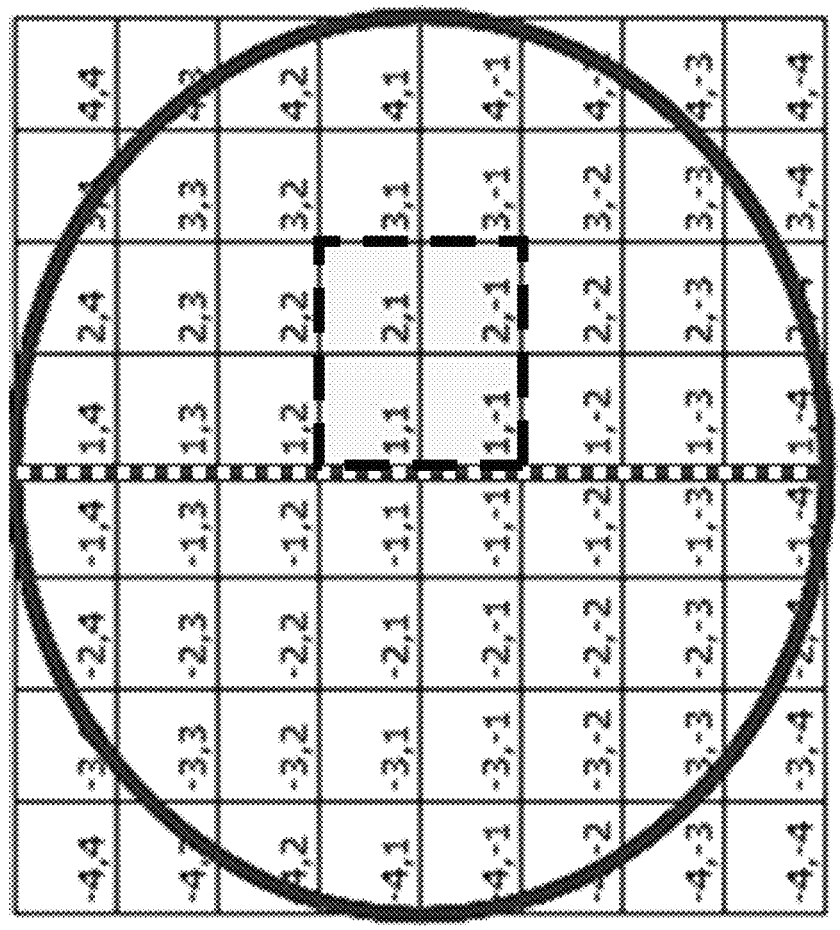
FIG. 8 is a diagram illustrating a plot area table of the position outputting process of the target according to the embodiment.

The position outputting process of the target according to the embodiment will be described along the flow diagram (Steps S1 to S10) of FIG. 3 with reference to FIGS. 4-8. FIG. 4 is a diagram illustrating a segmentation process of FIG. 3; FIG. 5 is a diagram illustrating a reference line specifying process and a center line specifying process of FIG. 3; FIG. 6 is a diagram illustrating a rotating process of FIG. 3; FIG. 7 is a diagram illustrating positions of a region center point and a target marker on a coordinate plane in the position outputting process of the target according to the embodiment; and FIG. 8 is a diagram illustrating a plot area table of the position outputting process of the target according to the embodiment.

First, segmentation of the ellipse region direction marker, the target marker, and the ellipse region is performed (Step S1). Specifically, the image segmentation is performed on the ellipse region direction marker (e.g., a spine of the fetus), the target marker (e.g., the cardiac position of the fetus), and the ellipse region (e.g., the body of the fetus) in an ultrasound image represented by a reference sign B1 of FIG. 4 by means of machine learning as indicated by a reference sign B2.

Then, two points are determined through which a reference line that passes through the center of gravity of the ellipse region direction marker and that equally divides the area of the ellipse region into two (i.e., halves the area of the ellipse region) passes (Step S2). In FIG. 5, as shown by a reference sign C1, the reference line indicated by a broken line is specified on the X- and Y-axes plane.

Intersections #1 at which the reference line intersects with the outer circumference of the ellipse region are determined (Step S3). In FIG. 5, two intersections #1 are specified as indicated by reference signs C2 and C3.

An ellipse-region center point between the two intersections of the reference line and the ellipse region is obtained (Step S4). In FIG. 5, the ellipse-region center point is specified as indicated by a reference sign C4.

A center line that is orthogonal to the reference line at the ellipse-region center point is determined (Step S5). In FIG. 5, as indicated by a reference sign C5, the center line represented by a thick line is specified.

Intersections #2 at which the center line intersects with the outer circumference of the ellipse region are determined (Step S6). In FIG. 5, two intersections #2 are specified as indicated by a reference sign C6.

Then, grid lines #1 that equally divide the reference line within the outer circumference of the ellipse region into n are determined (Step S7). In FIG. 5, as indicated by a reference sign C7, nine grid lines #1 including the center line and represented by one-dotted chain lines are specified.

In addition, grid lines #2 that equally divide the center line within the outer circumference of the ellipse region into m are determined (Step S8). In FIG. 5, as indicated by a reference sign C8, nine grid lines #2 represented by dotted lines and including the reference line are specified.

The grid lines #1 and #2, target points, and the like are rotated such that the reference line comes to be parallel to the Y-axis (Step S9). Specifically, the reference line represented by a broken line with a reference sign D1 of FIG. 6 is rotated, and the grid lines #1 and #2, the target points, and the like are rotated such that the reference line comes to be parallel to the Y-axis as indicated by a reference sign D2.

The coordinates at which the target marker is positioned are specified (Step S10). In FIG. 7, under a state where the grid lines are parallel to the X-axis or the Y-axis, the positions of the target marker and the region center point are specified. Then, the position outputting process of the target ends. In FIG. 8, the position of the target marker is displayed in a plot area table. As indicated by a broken-line frame, the example of FIG. 8 displays the target marker positioned in an area defined by the coordinates (1, 1), (2, 1), (1, −1), and (2, −1).

Figure 9:
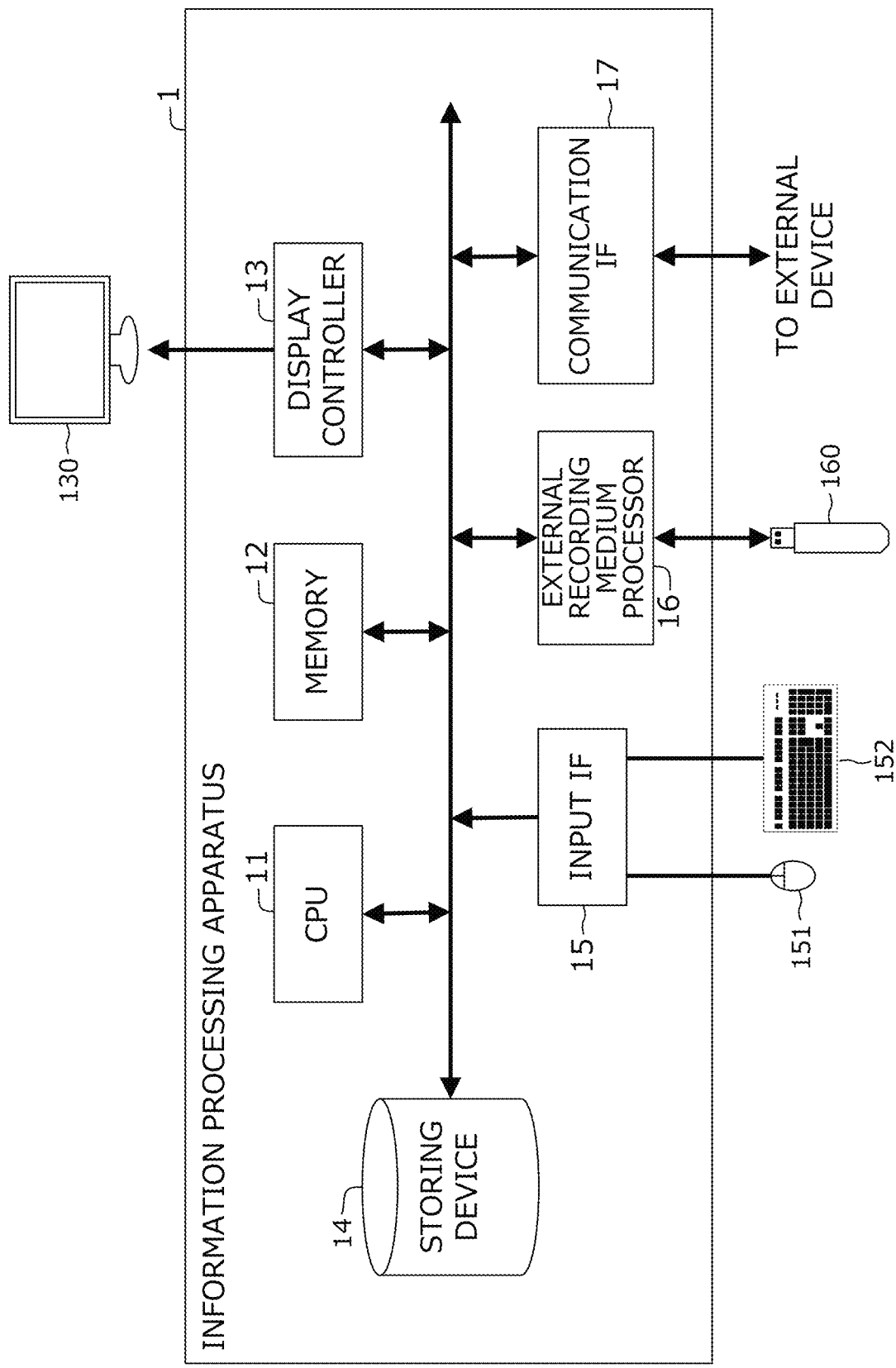
FIG. 9 is a block diagram schematically illustrating an example of an hardware configuration of an information processing apparatus of the embodiment.

FIG. 9 is a block diagram schematically illustrating an example of a hardware configuration of an information processing apparatus 1 of the embodiment.

As illustrated in FIG. 9, the information processing apparatus 1 includes a CPU 11, a memory 12, a display controller 13, a storing device 14, an input interface (IF) 15, an external recording medium processor 16, and a communication IF 17.

The memory 12 is an example of a storing unit, and is exemplified by a Read Only Memory (ROM) and a Random Access Memory (RAM). Into the ROM of the memory 12, a program such as a Basic Input/Output System (BIOS) may be written. The software program in the memory 12 may be appropriately read and executed by the CPU 11. The RAM of the memory 12 may be used as a temporary recording memory or a working memory.

The display controller 13 is connected to a displaying unit 130 and controls the displaying unit 130. The displaying unit 130 is, for example, a LCD, an Organic Light-Emitting Diode (OLED) display, a Cathode Ray Tube (CRT) display, or an electronic paper display, and displays various types of information to the operator. The displaying unit 130 may be combined with an input device, and may be a touch panel.

Examples of the storing device 14 are a Dynamic Random Access Memory (DRAM), an SSD, a Storage Class Memory (SCM), and an HDD.

The input IF 15 may be connected to an input device such as a mouse 11 and/or a keyboard 152 and may control the input device such as the mouse 11 and/or the keyboard 152. The mouse 11 and the keyboard 152 are examples of the input device, and the operator makes various input operation through these input devices.

The external recording medium processor 16 is configured to be mountable with a recording medium 160. The external recording medium processor 16 is configured to read, under a state of being mounted with the recording medium 160, information stored in the recording medium 160. In this embodiment, the recording medium 160 is portable and is exemplified by a flexible disk, an optical disk, a magnetic disk, an optical-magnetic disk, or a semiconductor memory.

The communication IF 17 is an interface that enables the information processing apparatus 1 to communicate with an external device(s).

The CPU 11 is an example of a processor and is a processing apparatus that carries out various controls and arithmetic operations. The CPU 11 achieves various functions by executing an operating system (OS) and a program read into the memory 12.

The apparatus that controls the operation of the overall information processing apparatus 1 is not limited to the CPU 11, and may alternatively be either one of a Micro Processing Unit (MPU), a Digital Signal Processor (DSP), an Application Specific Integrated Circuit (ASIC), a Programmable Logic Device (PLD), and a Field Programmable Gate Array (FPGA). The apparatus that controls the operation of the overall information processing apparatus 1 may be a combination of two or more of a CPU, an MPU, a DSP, an ASIC, a PLD, and an FPGA.

FIG. 10 is a block diagram schematically illustrating an example of a software configuration of the information processing apparatus 1 of FIG. 9.

The CPU 11 of the information processing apparatus 1 functions as a region specifying unit 111, a first straight-line specifying unit 112, a second straight-line specifying unit 113, and an outputting unit 114.

The region specifying unit 111 specifies the positions of the ellipse region direction marker, the target marker, and the ellipse region by image segmentation. In other words, the region specifying unit 111 specifies regions corresponding to a recess-free shape, and a detection target and a reference object included in the recess-free shape from a nondestructive inspection image.

The first straight-line specifying unit 112 specifies the reference line and the grid lines #2 parallel to the reference line. In other words, the first straight-line specifying unit 112 specifies a first straight line (in other words, the reference line) that equally divides the region corresponding to the recess-free shape into two and that passes through the region corresponds to the reference object. The first straight-line specifying unit 112 may specify multiple second grid lines (in other words, the grid lines #2) that equally divide the second line (i.e., the center line) within the outer circumference of the recess-free shape into m (where m is a natural number of two or more).

The second straight-line specifying unit 113 specifies the center line and the grid lines #1 parallel to the center line. In other words, the second-straight line specifying unit 113 determines the two intersection of the first straight line (in other words, the reference line) and the outer circumference of the recess-free shape, and specifies a second straight line (i.e., the center line) that passes through the center point of the determined two intersections and that is orthogonal to the first straight line. The second straight-line specifying unit 113 may specify multiple first grid lines (in other words, the grid lines #1) that equally divide the first straight line within the outer circumference of the recess-free shape into n (where n is a natural number of two or more).

The outputting unit 114 rotates the coordinate plane, and outputs the coordinates on which the target marker is positioned. In other words, using the coordinate system using the first straight line and the second straight line as the axes, the outputting unit 114 outputs information indicating the position of the detection target in the nondestructive inspection image. The outputting unit 114 may output the information indicative of the position of the detection target after rotating the recess-free shape such that the first straight line comes to be parallel to one of the axes a predetermined axis of the coordinate system. The output unit 114 may output the information indicative of the position of the detection target in the coordinate system in a grid shape formed by the multiple first grid lines and the multiple second grid lines.

<B> Effects

Hereinafter, effects that can be achieved by the information processing program, the information processing apparatus 1, and the method for processing information according to the embodiment will now be described.

The region specifying unit 111 specifies the regions corresponding to the recess-free shape, and the detection target and the reference object included in the recess-free shape from the nondestructive inspection image. The first straight-line specifying unit 112 divides the region corresponding to the recess-free shape into two segments and specifies the first straight line passing through the region corresponding to the reference object.

The second-straight line specifying unit 113 obtains the two intersections of the first straight line and the outer circumference of the recess-free shape, and specifies the second straight line that passes through the center point of the determined two intersections and that is orthogonal to the first straight line. Using the coordinate system using the first straight line and the second straight line as the axes, the outputting unit 114 outputs information indicative of the position of the detection target in the nondestructive inspection image. With this configuration, the soundness of the object of an inspection target can be precisely evaluated.

The outputting unit 114 outputs the information indicative of the position of the detection target after rotating the recess-free shape such that the first straight line comes to be parallel to one of the axes of the coordinate system. This makes it easier for the inspector to recognize the position of the detection target.

The second straight specifying unit 113 specifies the multiple first grid lines that equally divide the first line within the outer circumference of the recess-free shape into n (where, n is a natural number of two or more). The first straight specifying unit 112 specifies the multiple second grid lines that equally divide the second line within the outer circumference of the recess-free shape into m (where, m is a natural number of two or more). The output unit 114 may output information indicative of the position of the detection target in the coordinate system in a grid shape formed by the multiple first grid lines and the multiple second grid lines. Consequently, the position of the inspection target object is output on the plot area table, so that the inspector can easily recognize the position of the detection target.

The recess-free shape is a fetus, the detection target is a heart of the fetus, and the reference object is a spine of the fetus. As a result, the soundness and the like of the heart of the fetus can be precisely evaluated.

<C> Miscellaneous

The disclosed techniques are not limited to the embodiment described above, and may be variously modified without departing from the scope of the present embodiment. The respective configurations and processes of the present embodiment can be selected, omitted, and combined according to the requirement.

In the embodiment described above, the position outputting process of a target is performed on the image acquired by the ultrasonic inspection of a heart of a fetus, but the target of the position outputting process is not limited to this. The position outputting process of a target may be performed on the heart of an adult or a fetus, or may be performed on various organs and the like in various organisms including humans. Alternatively, the position output processing of a target may be applied to an internal inspection of a housing of a product at the time of factory shipment, periodic inspection, or the like.

A method used for capturing images is not limited to ultrasonography, and may alternatively use various nondestructive inspections such as a Magnetic Resonance Imaging (MRI) inspection, a Computed Tomography (CT) inspection, and a mammography inspection.

In one aspect, the soundness or the like of the object of the inspection target can be precisely evaluated.

In the claims, the indefinite article "a" or "an" does not exclude a plurality.

All examples and conditional language recited herein are intended for the pedagogical purposes of aiding the reader in understanding the invention and the concepts contributed by the inventor to further the art, and are not to be construed limitations to such specifically recited examples and conditions, nor does the organization of such examples in the specification relate to a showing of the superiority and inferiority of the invention. Although one or more embodiments of the present inventions have been described in detail, it should be understood that the various changes, substitutions, and alterations could be made hereto without departing from the spirit and scope of the invention.

What is claimed is:

1. A non-transitory computer-readable recording medium having stored therein an information processing program for causing a computer to execute a process comprising:
    specifying a first region, a second region and a third region from a nondestructive inspection image, the first region corresponding to a recess-free shape, the second region corresponding to a detection target included in the recess-free shape, the third region corresponding to a reference object included in the recess-free shape;
    specifying a first straight line that divides the first region into two and that passes through the third region;
    obtaining two intersections of the first straight line and an outer circumference of the recess-free shape;
    specifying a second straight line that passes through a center point of the two intersections and that is orthogonal to the first straight line;
    specifying a plurality of first grid lines that divide the first straight line within the outer circumference of the recess-free shape into n (where, n is a natural number of two or more);
    specifying a plurality of second grid lines that divide the second straight line within the outer circumference of the recess-free shape into m (where, m is a natural number of two or more); and
    outputting information indicative of a position of the detection target in a coordinate system being in a grid shape formed by the plurality of first grid lines and the plurality of second grid lines.

2. The non-transitory computer-readable recording medium according to claim 1, wherein the process further comprises outputting the information indicative of the position of the detection target after rotating the recess-free shape such that the first straight line comes to be parallel to an axis of the coordinate system.

3. The non-transitory computer-readable recording medium according to claim 2, wherein:
    the recess-free shape is a fetus;
    the detection target is a heart of the fetus; and
    the reference object is a spine of the fetus.

4. The non-transitory computer-readable recording medium according to claim 1, wherein:
    the recess-free shape is a fetus;
    the detection target is a heart of the fetus; and
    the reference object is a spine of the fetus.

5. An information processing apparatus comprising:
    a memory; and
    a processor coupled to the memory, the processor being configured to:
        specify a first region, a second region and third region from a nondestructive inspection image, the first region corresponding to a recess-free shape, the second region corresponding to a detection target included in the recess-free shape, the third region corresponding to a reference object included in the recess-free shape from a nondestructive inspection image;
        specify a first straight line that divides the first region into two and that passes through the third region;
        obtain two intersections of the first straight line and an outer circumference of the recess-free shape;
        specify a second straight line that passes through a center point of the two intersections and that is orthogonal to the first straight line;
        specify a plurality of first grid lines that divide the first straight line within the outer circumference of the recess-free shape into n (where, n is a natural number of two or more);
        specify a plurality of second grid lines that divide the second straight line within the outer circumference of the recess-free shape into m (where, m is a natural number of two or more); and
        output information indicative of a position of the detection target in a coordinate system being in a grid shape formed by the plurality of first grid lines and the plurality of second grid lines.

6. The information processing apparatus according to claim 5, wherein the processor is further configured to output the information indicative of the position of the detection target after rotating the recess-free shape such that the first straight line comes to be parallel to one of the axes of the coordinate system.

7. The information processing apparatus according to claim 6, wherein:
    the recess-free shape is a fetus;
    the detection target is a heart of the fetus; and
    the reference object is a spine of the fetus.

8. The information processing apparatus according to claim 5, wherein:
    the recess-free shape is a fetus;
    the detection target is a heart of the fetus; and
    the reference object is a spine of the fetus.

9. A computer-implemented method for processing information comprising
    specifying a first region, a second region and third region from a nondestructive inspection image, the first region corresponding to a recess-free shape, the second region corresponding to a detection target included in the recess-free shape, the third region corresponding to a reference object included in the recess-free shape from a nondestructive inspection image;
    specifying a first straight line that divides the first region into two and that passes through the third region;
    obtaining two intersections of the first straight line and an outer circumference of the recess-free shape;
    specifying a second straight line that passes through a center point of the two intersections and that is orthogonal to the first straight line;
    specifying a plurality of first grid lines that divide the first straight line within the outer circumference of the recess-free shape into n (where, n is a natural number of two or more);
    specifying a plurality of second grid lines that divide the second straight line within the outer circumference of the recess-free shape into m (where, m is a natural number of two or more); and outputting information indicative of a position of the detection target in a coordinate system being in a grid shape formed by the plurality of first grid lines and the plurality of second grid lines.

10. The computer-implemented method according to claim 9, wherein the method further comprises outputting the information indicative of the position of the detection target after rotating the recess-free shape such that the first straight line comes to be parallel to an axis of the coordinate system.

11. The computer-implemented method according to claim 9, wherein:
the recess-free shape is a fetus;
the detection target is a heart of the fetus; and
the reference object is a spine of the fetus.

* * * * *